(12) United States Patent
Koch

(10) Patent No.: US 9,622,905 B2
(45) Date of Patent: Apr. 18, 2017

(54) THERMOTHERAPY DEVICE WITH DETECTION OF AN OBLIQUELY POSITIONED RECLINING SURFACE

(71) Applicant: Dräger Medical GmbH, Lübeck (DE)

(72) Inventor: Jochim Koch, Ratzeburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 930 days.

(21) Appl. No.: 13/937,491

(22) Filed: Jul. 9, 2013

(65) Prior Publication Data

US 2014/0018887 A1  Jan. 16, 2014

(30) Foreign Application Priority Data

Jul. 11, 2012 (DE) .................. 10 2012 013 799

(51) Int. Cl.
*A61F 7/00* (2006.01)
*A61F 7/08* (2006.01)
*A61N 5/06* (2006.01)

(52) U.S. Cl.
CPC .............. *A61F 7/08* (2013.01); *A61N 5/0625* (2013.01); *A61N 2005/0626* (2013.01)

(58) Field of Classification Search
CPC ....... A61F 7/08; A61N 5/0625; A61N 5/0626; A61N 5/1069; A61N 5/107
See application file for complete search history.

(56) References Cited

U.S. PATENT DOCUMENTS

| 4,832,029 | A | * | 5/1989 | Koch | ........................ | A61N 5/06 |
| | | | | | | 362/130 |
| 5,453,077 | A | * | 9/1995 | Donnelly | ................ | A61G 11/00 |
| | | | | | | 600/22 |
| 5,759,149 | A | * | 6/1998 | Goldberg | ............. | A61M 16/109 |
| | | | | | | 600/22 |
| 6,063,020 | A | * | 5/2000 | Jones | ..................... | A61G 11/00 |
| | | | | | | 600/22 |
| 6,506,147 | B2 | * | 1/2003 | Eustace | ................... | A61G 11/00 |
| | | | | | | 600/22 |

(Continued)

FOREIGN PATENT DOCUMENTS

| DE | 20 2006 017 424 U1 | 12/2007 |
| DE | 10 2010 020 782 A1 | 11/2011 |
| JP | 2005 287 832 A | 10/2005 |

*Primary Examiner* — Kaitlyn Smith
(74) *Attorney, Agent, or Firm* — McGlew and Tuttle, P.C.

(57) ABSTRACT

A thermotherapy device with a reclining surface (6) for a patient and with two radiant heaters (3, 4) directed towards the reclining surface (6) and with a control unit (5), which is set up to control the heat output of each of the radiant heaters (3, 4). The reclining surface (6) includes structure for pivoting about an axis of rotation (12) at right angles to a body axis (11) of the patient. An angle or slope sensor (13) detects the deviation of the position of the reclining surface (6) from the horizontal plane. The control unit (5) is connected to the angle or slope sensor and adapts the heat output of each of the first radiant heater and of the second radiant heater (4) as a function of the detected measured value of the slope such that the heat output of each heater differs by a predetermined factor and the heat output of each heater is equal when the reclining surface is in the horizontal position.

12 Claims, 2 Drawing Sheets

(56) References Cited

U.S. PATENT DOCUMENTS

| | | | | |
|---|---|---|---|---|
| 6,746,394 | B2* | 6/2004 | Donnelly | A61F 7/00 |
| | | | | 600/22 |
| 7,008,371 | B2* | 3/2006 | Goldberg | A61M 16/109 |
| | | | | 600/22 |
| 2006/0163496 | A1 | 7/2006 | Hiramoto et al. | |
| 2007/0215819 | A1 | 9/2007 | Hiramoto et al. | |
| 2009/0177257 | A1* | 7/2009 | Khodak | A61G 11/00 |
| | | | | 607/96 |

* cited by examiner

THERMOTHERAPY DEVICE WITH DETECTION OF AN OBLIQUELY POSITIONED RECLINING SURFACE

CROSS REFERENCE TO RELATED APPLICATIONS

This application claims the benefit of priority under 35 U.S.C. §119 of German Patent Application DE 10 2012 013 799.0 filed Jul. 11, 2012, the entire contents of which are incorporated herein by reference.

FIELD OF THE INVENTION

The present invention pertains to a thermotherapy device with a reclining surface for accommodating a patient and a radiant heater for irradiating the reclining surface.

BACKGROUND OF THE INVENTION

A thermotherapy device with a reclining surface and with a radiant heating means is known from DE 20 2006 017 424 U1. An infrared lamp is provided as a radiant heater and a control means is used to control the radiant energy radiated by the radiant heater. The distance between the heating means and a test subject, who is located on the reclining surface, is detected by means of a distance-measuring means. The control means is designed such that a preselected radiation density becomes established on a reference surface, which is preferably arranged at or near the object, at a given distance from the test subject. The radiation output of the radiant heater is changed on the basis of the distance signal of the distance-measuring means such that the preselected radiation density on the reference surface remains essentially constant.

The drawback of the prior-art device is that the detection of the position of the test subject being irradiated in relation to the radiant heater by means of distance sensors is relatively complicated, because individual measured distance values are determined at first, and the angular offset of the reclining surface in relation to the radiant heater is then determined by linking individual measured values by means of a calculation formula. If the distance measurement is disturbed, because, for example, medical treatment procedures are carried out at the test subject, breathing tubes are displaced or brought inadvertently into the area detected by the distance-measuring means, incorrect setting may result at the radiant heater and a nonuniform radiation density becomes established.

SUMMARY OF THE INVENTION

A basic object of the present invention is to improve a device of the type described above in respect to the detection of the oblique position of the reclining surface in such a way that the most uniform irradiation possible of the test subject is achieved.

According to the invention, a thermotherapy device is provided comprising a reclining surface for accommodating a test subject in a body axis direction, a first radiant heater in an area of a head end of the test subject on the reclining surface and a second radiant heater in an area of the foot end of the test subject on the reclining surface. A bracket extends in the body axis direction and is arranged above the reclining surface. The bracket receives the first radiant heater in the area of the head end of the test subject and the second radiant heater in the area of the foot end of the test subject. A pivot means is associated with the reclining surface for pivoting the reclining surface about an axis of rotation that is at right angles to the body axis. An angle or slope sensor detects a deviation of a position of the reclining surface from a horizontal plane to detect a slope measured value. A control unit is connected to the angle or slope sensor and is connected to the first radiant heater and the second radiant heater and sets a heat output of each of the first radiant heater and the second radiant heater as a function of the detected slope measured value, whereby the heat output of each of the first radiant heater and the second radiant heater differs by a preset factor and are equal when the reclining surface is in a horizontal position.

The reclining surface is mounted pivotably and is connected to a fixed support, with the axis of rotation of the reclining surface extending at right angles to the direction of the axis of the test subject's body. A bracket, which extends in the direction of the axis of the test subject's body and which receives at least two infrared radiators, wherein a first infrared radiator is arranged in the area of the head end of the test subject and the second infrared radiator is arranged at the foot end. An infrared or radiant heater comprises a radiation body and a reflector each, which transmit their radiation output in the infrared spectrum. The reclining surface may be rotated such that either the distance between the first infrared radiation and the test subject is reduced and the distance between the second infrared radiator and the test subject is correspondingly increased, or there is an increase in the distance in the area of the first infrared radiator in case of a tilting of the reclining surface in the opposite direction.

Provisions are made according to the present invention for detecting the change in the position of the reclining surface with an angle or slope sensor, which determines the deviation of the reclining surface in relation to the horizontal. Since the angle or slope sensor is arranged in a fixed position at the reclining surface or in the connection area between the reclining surface and the support and the deviation of the position of the reclining surface in relation to the support is measured, care procedures, which are performed above the reclining surface, cannot compromise the measurement. The oblique position of the reclining surface in relation to a horizontal plane is detected by means of the angle or slope sensor and the radiation of the heat output of the first radiant heater to the heat output of the second radiant heater is adapted such that variation of the intensity of the heat radiation over the reclining surface is minimal. The distance between the radiant heaters and the reclining surface is, on average, about 800 mm. The distance between the radiant heaters is in a range around 400 mm. The radiant heaters have a connect load of 300 W each. The slope angle of the reclining surface equals approximately ±15° to a maximum of ±20°. The specific heat output is approximately 30 mW/cm$^2$. The uniformity of distribution of the radiation output is measured corresponding to IEC 60601-2-21 in temperature differences between the test objects. A uniformity of about 0.6° C. can be achieved with this concept between the center of the reclining surface and the outer test objects, even with the reclining surface in an oblique position. Suitable angle or slope sensors are angle transducers, which are fastened to the support or in the connection area between the support and the reclining surface and mechanically or optically detect the rotation of the reclining surface about the axis of rotation thereof.

Furthermore, provisions may also be made in case of open care to adjust the reclining surface upwardly in order to offer better access to the child as a result. The control unit is set up to detect the height adjustment of the reclining surface by means of a path sensor and to adapt the heat output of the first radiant heater and of the second radiant heater as a function of the adjusted height such that a previously set intensity distribution of the heat output over the reclining surface remains essentially unchanged.

An exemplary embodiment of the device according to the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
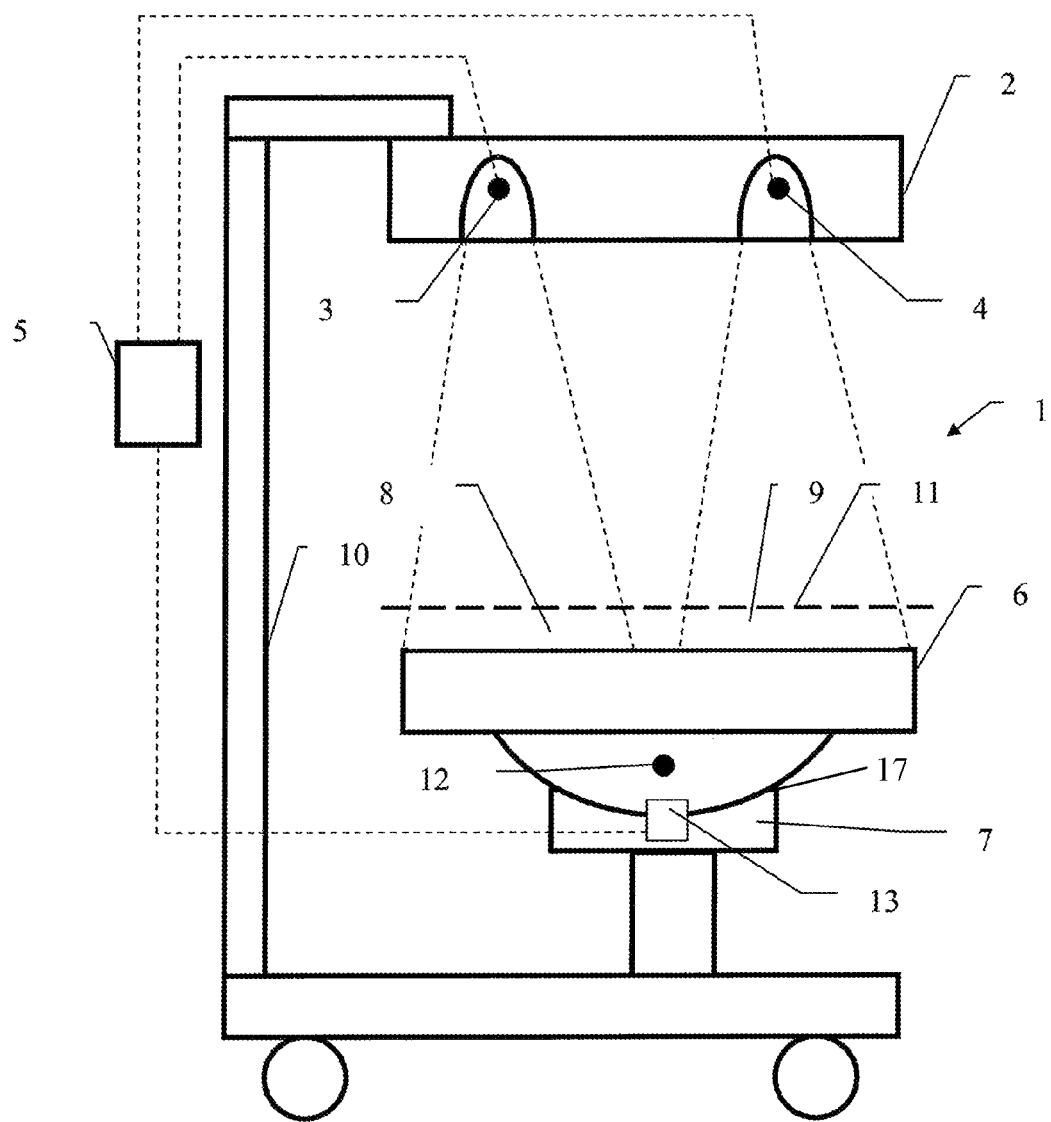
FIG. 1 is a side schematic view showing a thermotherapy device with a pivotable reclining surface.

Referring to the drawings in particular, FIG. 1 shows a first thermotherapy device 1, which has a bracket 2 for mounting a first radiant heater (a head side area radiant heater) 3 and a second radiant heater (a foot side area radiant heater) 4. Bracket 2 is located above a reclining surface 6, on which a patient, not shown in more detail, is located, and which can be pivoted into a head up position and into a head down position. The head end 8 is located in the area of a vertical carrier 10, to which bracket (support) 2 for the radiant heaters 3, 4 is attached. The foot end 9 is arranged in the area of the second radiant heater 4. The adjustment of the reclining surface 6 in relation to a support 7 can be performed either manually or automatically. The bracket (support) 2, the support 7 and the floor engagement structure (which is shown as a support platform with wheels) are part of a support structure. The patient, not shown in more detail, is located on the reclining surface 6 along a body axis 11. A manually or automatically actuated pivot connection (pivot device-pivot means) 17 is associated with the reclining surface 6 for pivoting the reclining surface about an axis of rotation that is at right angles to the body axis, such that the adjustment of the reclining surface 6 in relation to the support 7 is performed about an axis of rotation 12. The body axis 11 and the axis of rotation 12 are at right angles to one another. The position of the reclining surface 6 in relation to support 7 is detected by means of an angle transducer 13 and sent to a control unit 5, which supplies the first radiant heater 3 and the second radiant heater 4 with electricity. The electric power of the radiant heaters 3, 4 is controlled as a function of the oblique position of the reclining surface 6 such that a uniform radiation distribution is achieved for all oblique positions. The first radiant heater 3 and the second radiant heater 4 are designed in terms of radiation technology such that they irradiate the reclining surface 6 uniformly if the reclining surface 6 is directed horizontally. Both radiant heaters 3, 4 are operated with equal electric power for this case. In case of the head up position, for example, the first radiant heater 3, which irradiates mainly the surface in the head area 8, is operated with less power, whereas the second radiant heater 4 at the foot end 9 is operated with a somewhat higher power, so that a highly uniform radiation distribution is achieved on the reclining surface 6 even in case of an oblique position.

Figure 2:
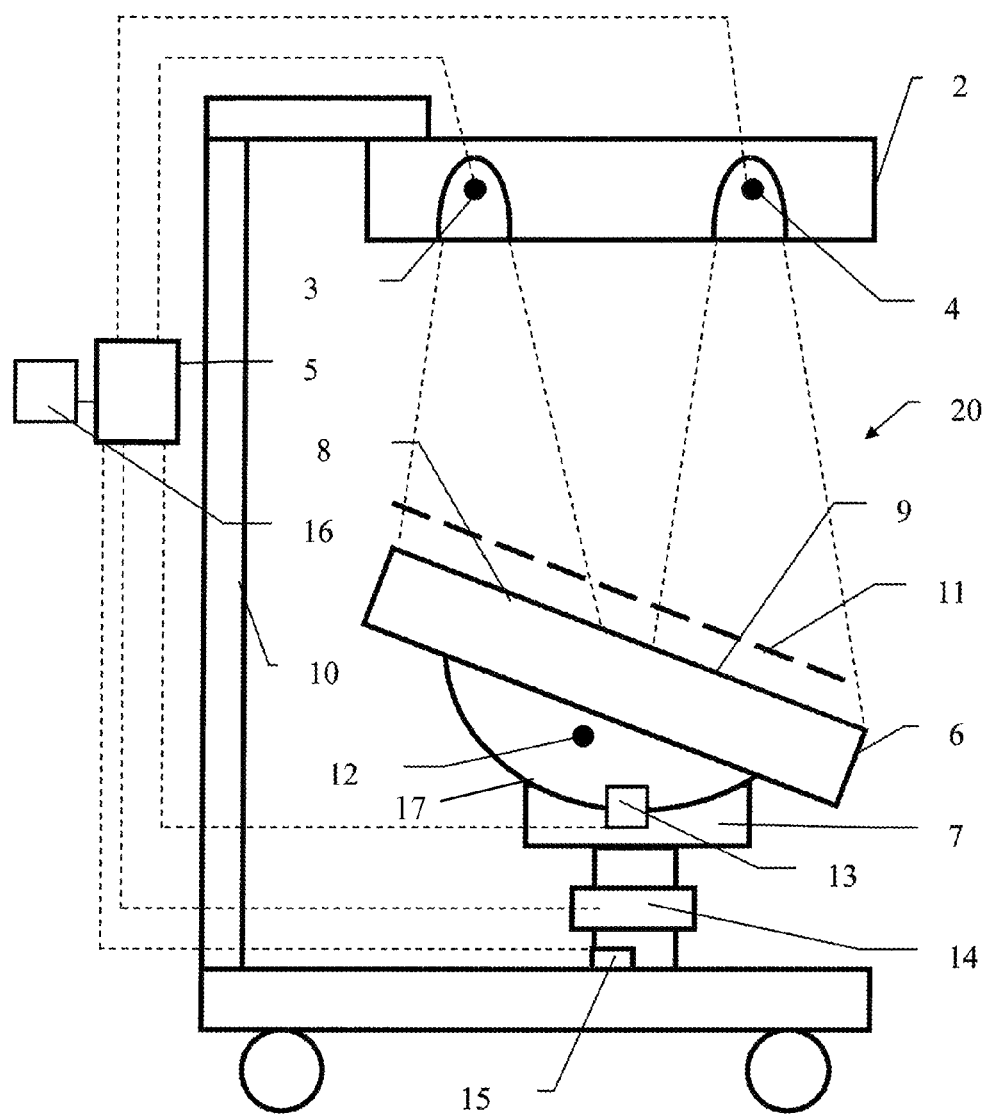
FIG. 2 is a side schematic view showing the thermotherapy device according to FIG. 1 with obliquely positioned reclining surface and height adjustment of the reclining surface.

FIG. 2 shows a second thermotherapy device 20, which additionally has a lifting device—lifting means 14 at the support 7 for the reclining surface 6 compared to the first thermotherapy device 1 according to FIG. 1. The reclining surface 6 can be raised or lowered with the lifting means 14. The height adjustment of the reclining surface 6 is detected by a path sensor 15. The lifting means 14 and the path sensor 15 are connected to the control unit 5. The reclining surface 6 can be pivoted by means of an operating unit 16 connected to the control unit 5 to automatically actuate pivot connection (pivot means) 17 and may be height adjusted by means of an operating unit 16 connected to the control unit 5 to automatically actuate the lifting means 14. The radiation outputs of the radiant heaters 3, 4 are also correspondingly adapted in case of a height adjustment of the reclining surface 6. The radiation outputs of the radiant heaters are reduced in case the reclining surface is raised and they are increased if the reclining surface is lowered. The reclining surface 6 is in the head up position in the second thermotherapy device 20 shown in FIG. 2. The angle transducer 13 detects the change in the position of the reclining surface 6 in relation to the horizontal and control unit 5 correspondingly reduces the radiation output of the first radiant heater 3 and increases the radiation output emitted by the second radiant heater 4.

While specific embodiments of the invention have been shown and described in detail to illustrate the application of the principles of the invention, it will be understood that the invention may be embodied otherwise without departing from such principles.

What is claimed is:

1. A thermotherapy device comprising:
   a reclining surface for accommodating a patient in a body axis direction;
   a first radiant heater in an area of a head end of the patient on the reclining surface;
   a second radiant heater in an area of the foot end of the patient on the reclining surface;
   a bracket extending in the body axis direction and arranged above the reclining surface, the bracket receiving the first radiant heater in the area of the head end of the patient and the second radiant heater in the area of the foot end of the patient;
   a pivot means associated with the reclining surface for pivoting the reclining surface about an axis of rotation that is at right angles to the body axis;
   an angle or slope sensor detecting a deviation of a position of the reclining surface from a horizontal plane to detect a slope measured value; and
   a control unit connected to the angle or slope sensor and connected to the first radiant heater and the second radiant heater and setting a heat output of each of the first radiant heater and the second radiant heater as a function of the detected slope measured value, whereby the heat output of each of the first radiant heater and the second radiant heater differs by a preset factor and are equal when the reclining surface is in a horizontal position.

2. A thermotherapy device in accordance with claim 1, wherein the preset factor is selected such that a variation of an intensity of the heat output over the reclining surface is minimal.

3. A thermotherapy device in accordance with claim 1, wherein:
the pivot means is part of a support for the reclining surface;
the angle or slope sensor comprises an angle transducer, which is fastened to the support or in a connection area between the support and the reclining surface; and
the angle transducer provides a mechanical or optical detection of the slope of the reclining surface.

4. A thermotherapy device in accordance with claim 1, further comprising a lifting device for raising and lowering the reclining surface, wherein:
the lifting device is connected to the reclining surface and is connected to the control unit; and
the control unit is configured to act on the lifting device to adjustably move the reclining surface upwardly and downwardly by actuating the lifting means, whereby better access to the patient is provided.

5. A thermotherapy device in accordance with claim 4, further comprising a path sensor detecting a height adjustment of the reclining surface, wherein:
the path sensor is connected to the control unit; and
the control unit is configured to detect a height adjustment of the reclining surface via the path sensor and to adapt the heat output of the first radiant heater and the second radiant heater as a preset function of the height adjustment, such that a previously set intensity distribution of the heat output over the reclining surface remains essentially unchanged.

6. A thermotherapy device comprising:
a support structure;
a reclining surface having a length in a length direction and a width in a width direction, the reclining surface for accommodating a patient, the reclining surface being supported by the support structure;
a head side area radiant heater supported by the support structure;
a foot side area radiant heater supported by the support structure;
a pivot connection between the reclining surface and the support structure for pivoting the reclining surface relative to the support structure;
an angle or slope sensor detecting an angle or slope of the reclining surface and providing a detected angle or slope measured value; and
a control unit connected to the angle or slope sensor and connected to the head side area radiant heater and connected to the foot side area radiant heater and setting a heat output of each of the head side area radiant heater and the foot side area radiant heater as a function of the detected slope measured value.

7. A thermotherapy device in accordance with claim 6, wherein the support structure comprises a bracket extending in the length direction and arranged above the reclining surface, the bracket receiving the head side area radiant heater in the area of the head end of the patient and the second radiant heater in the area of the foot end of the patient.

8. A thermotherapy device in accordance with claim 6, wherein the control unit sets a heat output of each of the first radiant heater and the second radiant heater as a function of the detected angle or slope measured value such that the heat output of each of the head side area radiant heater and the foot side area radiant heater differs by a preset factor and are equal or substantially equal when the reclining surface is in a horizontal position wherein the preset factor is selected such that a variation of an intensity of the heat output over the reclining surface is minimal.

9. A thermotherapy device in accordance with claim 6, wherein:
the support structure includes a support for the reclining surface; and
the pivot connection is a part of or connected to the support for the reclining surface.

10. A thermotherapy device in accordance with claim 9, wherein:
the angle or slope sensor comprises an angle transducer, which is fastened to the support for the reclining surface or the pivot connection in a connection area between the support for the reclining surface and the reclining surface; and
the angle transducer provides a mechanical or optical detection of the slope of the reclining surface.

11. A thermotherapy device in accordance with claim 6, further comprising a lifting device connected to the reclining surface, connected to the support structure and connected to the control unit wherein the control unit acts on the lifting device to adjustably move the reclining surface upwardly and downwardly by actuating the lifting device, whereby better access to the patient is provided.

12. A thermotherapy device in accordance with claim 11, further comprising a path sensor detecting a height adjustment of the reclining surface, wherein:
the path sensor is connected to the control unit; and
the control unit detects a height adjustment of the reclining surface via the path sensor and adapts the heat output of the head side area radiant heater and the foot side area radiant heater as a preset function of the height adjustment, such that a previously set intensity distribution of the heat output over the reclining surface remains essentially unchanged.

* * * * *